United States Patent
Kageyama et al.

(10) Patent No.: US 7,927,649 B2
(45) Date of Patent: Apr. 19, 2011

(54) ORAL CAVITY STIMULATING SUBSTANCE

(75) Inventors: Norihiko Kageyama, Ibaraki (JP); Takako Inui, Ibaraki (JP); Koichi Nakahara, Toyonaka (JP); Hajime Komura, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 677 days.

(21) Appl. No.: 11/791,651

(22) PCT Filed: Nov. 29, 2005

(86) PCT No.: PCT/JP2005/021883
§ 371 (c)(1),
(2), (4) Date: Feb. 20, 2008

(87) PCT Pub. No.: WO2006/057406
PCT Pub. Date: Jun. 1, 2006

(65) Prior Publication Data
US 2009/0029006 A1    Jan. 29, 2009

(30) Foreign Application Priority Data
Nov. 29, 2004 (JP) .................... 2004-345004

(51) Int. Cl.
*A23K 1/00* (2006.01)
(52) U.S. Cl. .............. 426/615; 426/231; 426/536
(58) Field of Classification Search ............. 426/615, 426/618; 536/17.9, 53
See application file for complete search history.

(56) References Cited

U.S. PATENT DOCUMENTS
3,475,459 A    10/1969    Stoessl

FOREIGN PATENT DOCUMENTS
| | | |
|---|---|---|
| JP | 3390770 | 1/2003 |
| JP | 2003-342187 | 12/2003 |
| WO | 2004/002978 | 1/2004 |

OTHER PUBLICATIONS

Office Action mailed Oct. 9, 2009 in Chinese application No. 200580040559.6 with partial English translation.
International Preliminary Report on Patentability issued May 30, 2007, in PCT/JP2005/021883 filed Jul. Nov. 29, 2005.
A. Stoessl, "The Antifungal Factors In Barley. IV . Isolation, Structure, and Synthesis of the Hordatines", Canadian Journal of Chemistry, Mar. 8, 1967, pp. 1745-1760, vol. 45, No. 15.
A. Stoessl, "The Antifungal Factors in Barley—The Constitutions of Hordatines A and B", Tetrahedron Letters, Feb. 25, 1966, pp. 2287-2292, No. 21, Pergamon Press Ltd., Printed in Great Britain.
Kim Burhenne et al., "A New Class Of N-Hydroxycinnamoyltransferases", The Journal of Biological Chemistry, Apr. 18, 2003, pp. 13919-13927, vol. 278, No. 16, Published by the American Society of Biochemistry and Molecular Biology, Inc., USA.
Translated by Koya Nakanishi et al., "Morrison Boyd Yuki Kagaku (Ge)", 5th Edition, Tokyo Kagaku Dojin, Mar. 1, 1990, pp. 1634-1637.
Kimiko Atake et al., "To Kagaku no Kiso", Kodansha Scientific, Aug. 10, 1995, pp. 85-88.
International Search Report dated Jan. 31, 2006 for PCT/JP2005/021883 filed Jul. Nov. 29, 2005.
Supplementary European Search Report mailed Feb. 19, 2008 issued in EP Application No. 05 81 1489.

*Primary Examiner* — Michael G Hartley
*Assistant Examiner* — Jagadishwar R Samala
(74) *Attorney, Agent, or Firm* — Drinker Biddle & Reath LLP

(57) ABSTRACT

A novel compound causing an oral cavity stimulus such as acridness, which is expressed by the following structural formula (I).

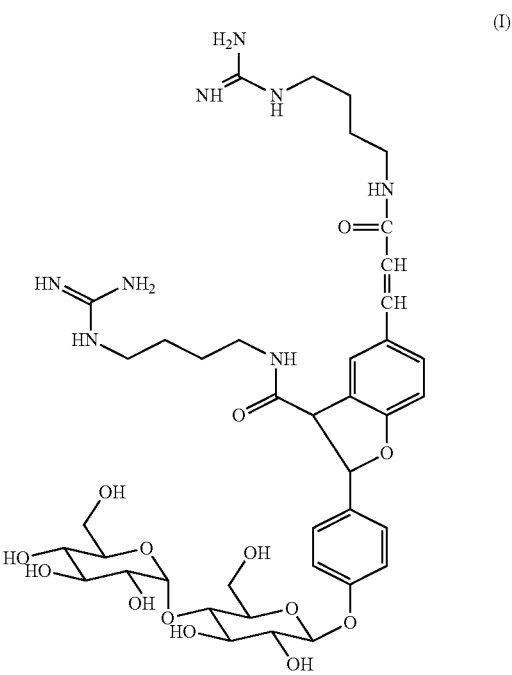

15 Claims, 11 Drawing Sheets

ORAL CAVITY STIMULATING SUBSTANCE

CROSS REFERENCE TO RELATED APPLICATIONS

Figure 1:
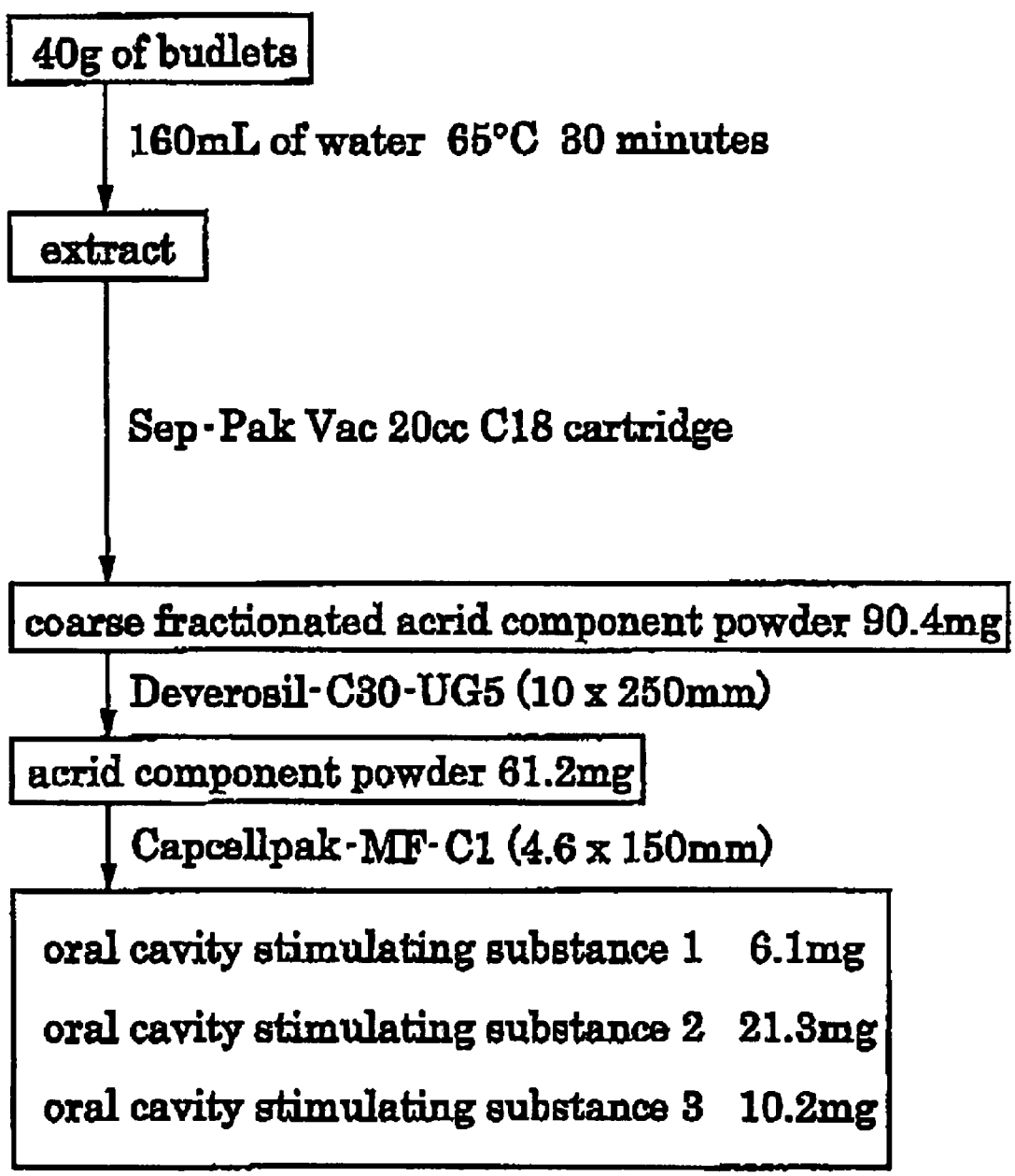

This application is the National Stage of International Application No. PCT/JP2005/021883, filed Nov. 29, 2005, which claims benefit of Japanese Application No. 2004-345004, filed Nov. 29, 2004, all of which are incorporated by reference in their entirety.

TECHNICAL FIELD

This invention relates to novel compounds (oral cavity stimulating substances).

BACKGROUND ART

A liking for flavor and taste relating to food varies from consumer to consumer, and can change constantly with age, for example. Moreover, with circulation of a wide variety of foods and foodstuffs accompanying the development of physical distribution of recent years, and increasing concern about the safety of food these days, the consumer's taste for food is changing quickly and becoming diversified today.

In response to such diversification of the consumer's taste, it has become imperative for the liquor and food industry to develop liquors and foods with various characteristics in order to expand the range of selection for the consumer. It is the present state, therefore, that goods that agree with the consumer's taste are being developed by selecting various raw materials and changing manufacturing conditions in order to create various flavors.

Such a situation is not an exception for the industry of alcoholic beverages and foods for which malt is used as the raw material (e.g. brewed beverages such as beer and happoshu (low-malt beer), distilled liquors such as whiskey, and confectionery such as pop sweets).

One of the flavors that the consumer can taste in suck alcoholic beverages and foods made from malt is what is called acridness. Acridness is a flavor (oral cavity stimulant) that is deeply related, in the case of beer drinks, to taste when taken into the mouth, through the throat, and to aftertaste. Conventionally, the substances leading to a stimulus in the oral cavity such as acridness (hereinafter called oral cavity stimulating substances) have been considered to be oxalic add and homogentisic acid in vegetables such as bamboo shoot and spinach (see Patent Document 1).

Patent document 1: Japanese Patent No. 3390770

DISCLOSURE OF THE INVENTION

Problem to be Solved by the Invention

There can be limitations to the method of developing goods that agree with the consumer's taste by changing raw materials and manufacturing conditions in order to cope with the consumer's diverse taste.

In manufacture of beer drinks, for example, available raw materials are limited by Liquor Tax Law (to malt, hop, rice and so on), thereby limiting selection of raw materials. In the case of changing manufacturing conditions, the changes may require new manufacturing facilities, thereby giving rise to a problem of equipment cost.

Therefore, since certain restrictions accompany changes in the raw material or manufacturing process, flavor that can be created will also be restricted. Even when there is a desire for manufacture of beer somewhat different from the conventional beer in "taste through the throat", for example, immense time, expense and labor may be required to make an attempt all from selection of raw materials to a change in the manufacturing process.

One of the problems of industrial products as a whole is the problem of quality control (homogeneity of products). Since agricultural products are the main raw materials for such food and drink products, the products are subject to variations of ingredients by the place of production and yearly output. The variations have a direct relationship to the flavors of products, thereby also to influence sales inevitably. Therefore, quality control is an especially important question for food or drink products also.

On the other hand, numerous researches and reports have been made up to the present regarding the components that influence flavor. For example, it has been known for years that certain types of amino acid give delicious taste to food. It has been practised to add glutamate to food and drink in order to enhance taste.

However, when the flavor of food and drink is adjusted in this way, it is essential that flavor components are identified. Therefore, also regarding the flavor called acridness which can influence the taste, throat feel, and aftertaste which are important for beer drinks, for example, it is essential to identify the substances leading thereto (oral cavity stimulating substances). However, such oral cavity stimulating substances in the liquors and foods that use malt as the raw material have not been identified.

This invention has been made having regard to the state of the art noted above, and its object is to identify new compounds leading to an oral cavity stimulus such as acridness.

Means for Solving the Problem

A first characteristic construction of this invention lies in a compound expressed by the following structural formula (I):

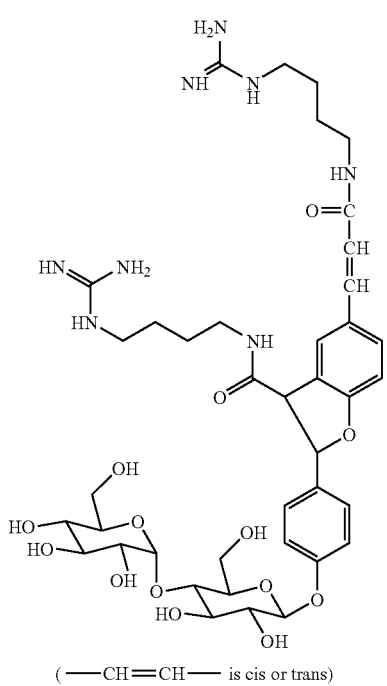

Chemical Formula 1

( ——CH═CH—— is cis or trans)

The chemical structure of the compound according to the first characteristic construction of this invention has the same skeleton as the chemical structure of a known biophylactic substance having antifungal capability called hordatine (U.S. Pat. No. 3,475,459). However, it is different from hordatine in that maltose is added to a phenolic hydroxyl group by β-glycosidic linkage. There has heretofore been no document reporting this chemical structure, and therefore the compound of this invention is a novel chemical substance.

A second characteristic construction of this invention lies in a compound expressed by the following structural formula (II):

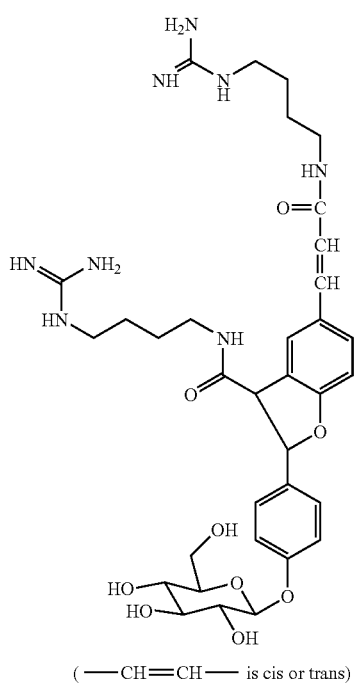

Chemical Formula 2

( —CH═CH— is cis or trans)

The chemical structure of the compound according to the second characteristic construction of this invention has the same skeleton as the chemical structure of a known biophylactic substance having antifungal capability called hordatine (U.S. Pat. No. 3,475,459). However, it is different from hordatine in that glucose is added to a phenolic hydroxyl group by β-glycosidic linkage. There has heretofore been no document reporting this chemical structure, and therefore the compound of this invention is a novel chemical substance.

A third characteristic construction of this invention lies in a compound expressed by the following structural formula (III):

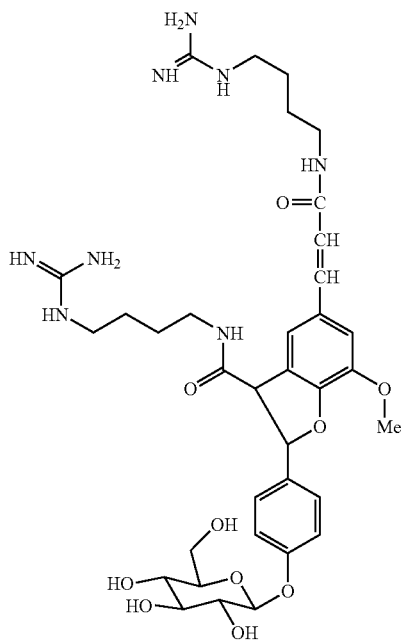

Chemical Formula 3

( —CH═CH— is cis or trans, and Me is a methyl group)

The chemical structure of the compound according to the third characteristic construction of this invention has the same skeleton as the chemical structure of a known biophylactic substance having antifungal capability called hordatine (U.S. Pat. No. 3,475,459). However, it is different from hordatine in that part of the structure corresponding to the benzofuran skeleton is modified by a methoxy group, and that glucose is added to a phenolic hydroxyl group, by β-glycosidic linkage. There has heretofore been no document reporting this chemical structure, and therefore the compound of this invention is a novel chemical substance.

A fourth characteristic construction of this invention lies in that the compounds, expressed by the above structural formulae (I)-(III) are oral cavity stimulating substances.

The compounds according to the fourth characteristic construction of this invention, when put to an organoleptic evaluation by trained examiners (panel), were confirmed to have a sharp acridness (oral cavity stimulus) remaining on the tongue. That is, the compounds of this invention are a type of oral cavity stimulating substance.

Therefore, it becomes possible to obtain and use the compounds of this invention as substances that cause an oral cavity stimulus such as acridness (oral cavity stimulating substance). That is, since the chemical structures are known, it is possible to consult, for example, a method of analyzing a known compound having a similar structure. Thus, a separating and refining method may be established for separating the compounds of this invention more efficiently from natural plants (e.g. malt) which may contain such compounds. Or they may be obtained directly by performing organic synthesis.

As a result, by using the compounds of this invention as additives, for example, in various foods and drinks, an oral cavity stimulus, especially a flavor called acridness, is newly given (or enhanced), to give such foods and drinks a profounder flavor or make them satisfying foods (or satisfying drinks). Further, by adjusting the quantity of addition, the degrees of such flavor and satisfactory eating (or satisfactory drinking) can be adjusted freely, to cope with the diversifying taste of the consumer promptly. That is, without going through the conventional development process requiring much time, expense and labor for efforts ranging from selection of raw materials to modification of manufacturing conditions, it is possible also to develop quickly and simply various products having various flavors (oral cavity stimulus such as acridness and others).

Further, since an assay of the compounds of this invention may also be established, the compounds of this invention may, for example, be quantified for products such as liquors and foods which use malt as raw material, and the manufacture process may be monitored. Thus, not only qualitatively performing quality control about a flavor called acridness by sample tasting, for example, but may be performed also quantitatively. In this way, quality control is performed with increased thoroughness to promise a further improvement in product quality.

A fifth characteristic construction of this invention lies in that the above oral cavity stimulating substances are derived from a sprouted cereal grain.

The compounds (oral cavity stimulating substances) according to the fifth characteristic construction of this invention are derived from a sprouted cereal grain (e.g. sprouted brown rice, sprouted wheat, sprouted barley, sprouted soybean or sprouted maize seed). Thus, the compounds (oral cavity stimulating substances) of this invention can be obtained by separating and refining such sprouted cereal grain. Since such sprout grain is relatively cheap and easily obtainable, it is also possible to ensure stable supply of the compounds of this invention industrially.

Many liquors and foods that use malt (sprouted barley) as raw material exist (e.g. brewed beverages such as beer and happoshu (low-malt beer), distilled beverages such as whiskey, and confectionery such as pop sweets). Such liquors and foods often have acrid taste. Therefore, where the compounds of this invention are derived from malt, the compounds of this invention may be added to liquors and foods that use malt as raw material. Then, in addition to the acridness inherent in such liquors and food, a more profound flavor and a feel of satisfactory eating (or satisfactory drinking) can be given easily. That is, adding the compounds of this invention derived from malt to beer drinks, for example, means an increase of the compounds of this invention contained from the first. Compared with the case of adding oral cavity stimulating substances derived from other raw materials (e.g. oxalic add, homogentisic acid and so on), the compounds of this invention can exist stably in the beer drinks, and never impart certain adverse influence on the other beer components to impair the original flavor of the beer. The taste, effect in the throat or aftertaste can be adjusted freely according to the consumer's taste.

A sixth characteristic construction of this invention lies in an oral cavity stimulating agent containing a compound according to the fourth characteristic construction.

With the oral cavity stimulating agent according to the sixth characteristic construction of this invention, since each of the compounds (oral cavity stimulating substances) according to the fourth characteristic construction has a peculiar oral cavity stimulus (acridness in particular), it is possible to give various oral cavity stimuli by using each of the oral cavity stimulating substances alone or in a desired combination. Therefore, by adding the oral cavity stimulating agent of this invention to food and drink, it will be possible to manufacture simply and quickly products of the same food and drink but having various oral cavity stimuli. Further, considering that the degree of oral cavity stimulus can be adjusted also with the quantity of addition, the range of variation of oral cavity stimulus will become very large, thereby to satisfy consumers having various tastes. For example, such an oral cavity stimulating agent may be used on the tables of ordinary homes as a seasoning, to enrich dietary life still further.

A seventh characteristic construction of this invention lies in an oral cavity stimulating agent containing a compound according to the fifth characteristic construction.

With the oral cavity stimulating agent according to the seventh characteristic construction of this invention, since each of the compounds (oral cavity stimulating substances) according to the fifth characteristic construction has a peculiar oral cavity stimulus (acridness in particular), it is possible to give various oral cavity stimuli by using each of the oral cavity stimulating substances alone or in a desired combination. Therefore, by adding the oral cavity stimulating agent of this invention to food and drink, it will be possible to manufacture simply and quickly products of the same food and drink but having various oral cavity stimuli. Further, considering that the degree of oral cavity stimulus can be adjusted also with the quantity of addition, the range of variation of oral cavity stimulus will become very large, thereby to satisfy consumers having various tastes. For example, such an oral cavity stimulating agent may be used on the tables of ordinary homes as a seasoning, to enrich dietary life still further. Since the above sprout grain is relatively cheap and easily obtainable, it is also possible to ensure stable supply of the compounds of this invention industrially.

An eighth characteristic construction of this invention lies in an acridity adding agent containing a compound according to the fourth characteristic construction.

With the acridity adding agent according to the eighth characteristic construction of this invention, since each of the compounds (oral cavity stimulating substances) according to the fourth characteristic construction has a peculiar acridness, it is possible to give various acridnesses by using each of the oral cavity stimulating substances alone or in a desired combination. Therefore, by adding the acridity adding agent of this invention to food and drink, it will be possible to manufacture simply and quickly products of the same food and drink but having various acridnesses. Further, considering that the degree of acridness can be adjusted also with the quantity of addition, the range of variation of acridness becomes very large, thereby to satisfy consumers having various tastes. For example, such an acridness adding agent may be used on the tables of ordinary homes as a seasoning, to enrich dietary life still further.

A ninth characteristic construction of this invention lies in an acridity adding agent containing a compound according to the fifth characteristic construction.

With the acridity adding agent according to the ninth characteristic construction of this invention, since each of the compounds (oral cavity stimulating substances) according to the fifth characteristic construction has a peculiar acridness, it is possible to give various acridnesses by using each of the oral cavity stimulating substances alone or in a desired combination. Therefore, by adding the acridity adding agent of this invention to food and drink, it will be possible to manufacture simply and quickly products of the same food and drink but having various acridnesses. Further, considering that the degree of acridness can be adjusted also with the quantity of addition, the range of variation of acridness becomes very large, thereby to satisfy consumers having various tastes. For example, such ah acridness adding agent may be used on the tables of ordinary homes as a seasoning, to enrich dietary life, still further. Since the above sprout grain is relatively cheap and easily obtainable, it is also possible to ensure stable supply of the compounds of this invention industrially.

A first characteristic means of this invention lies in a method of evaluating a degree of acridness of food and drink or a raw material thereof, using the content of any one compound among the compounds according to the first to third characteristic constructions, or the content of a mixture of said compounds, as an index.

With the evaluating method defined in the first characteristic means of this invention, the content of any one compound among the compounds according to the first to third characteristic constructions, or the content of a mixture of said compounds is used as an index of the degree of acridness. It is thus possible, for example, to prepare a standard solution containing said compound in a predetermined quantity, to measure the content of said compound in food and drink or in the raw material based on the standard solution, and to evaluate the degree of acridness by quantitative value. Therefore, simple, objective, and highly reliable evaluation results can be obtained without carrying out an organoleptic evaluation of acridness by many panelists as practised conventionally in order to obtain reliable results.

A tenth characteristic construction of this invention lies in a food or drink having added thereto at least one of the compounds according to the first to third characteristic constructions, the oral cavity stimulating substance according to the sixth or seventh characteristic construction, and the acridity adding agent according to the sixth of seventh characteristic construction.

The food or drink according to the tenth characteristic construction of this invention can be manufactured quickly and simply by adding to the food or drink at least one of the compounds according to the first to third characteristic constructions, the oral cavity stimulating substance according to the sixth or seventh characteristic construction, and the acridity adding agent according to the sixth or seventh characteristic construction. And a diverse variation of flavor (oral cavity stimulus such as acridness) can be given, thereby to satisfy diversifying tastes of the consumer promptly.

An eleventh characteristic construction of this invention lies in that said food or drink is an alcoholic beverage or a nonalcoholic beverage.

The food or drink according to the eleventh characteristic construction of this invention can satisfy diverse tastes of the consumer regarding alcoholic beverages or nonalcoholic beverages promptly.

A twelfth characteristic construction of this invention lies in that said alcoholic beverage is a malt fermented drink.

The food or drink according to the twelfth characteristic construction of this invention can satisfy diverse tastes of the consumer regarding malt fermented drinks (e.g. beer drinks) promptly.

BEST MODE FOR CARRYING OUT THE INVENTION

Figure 10:
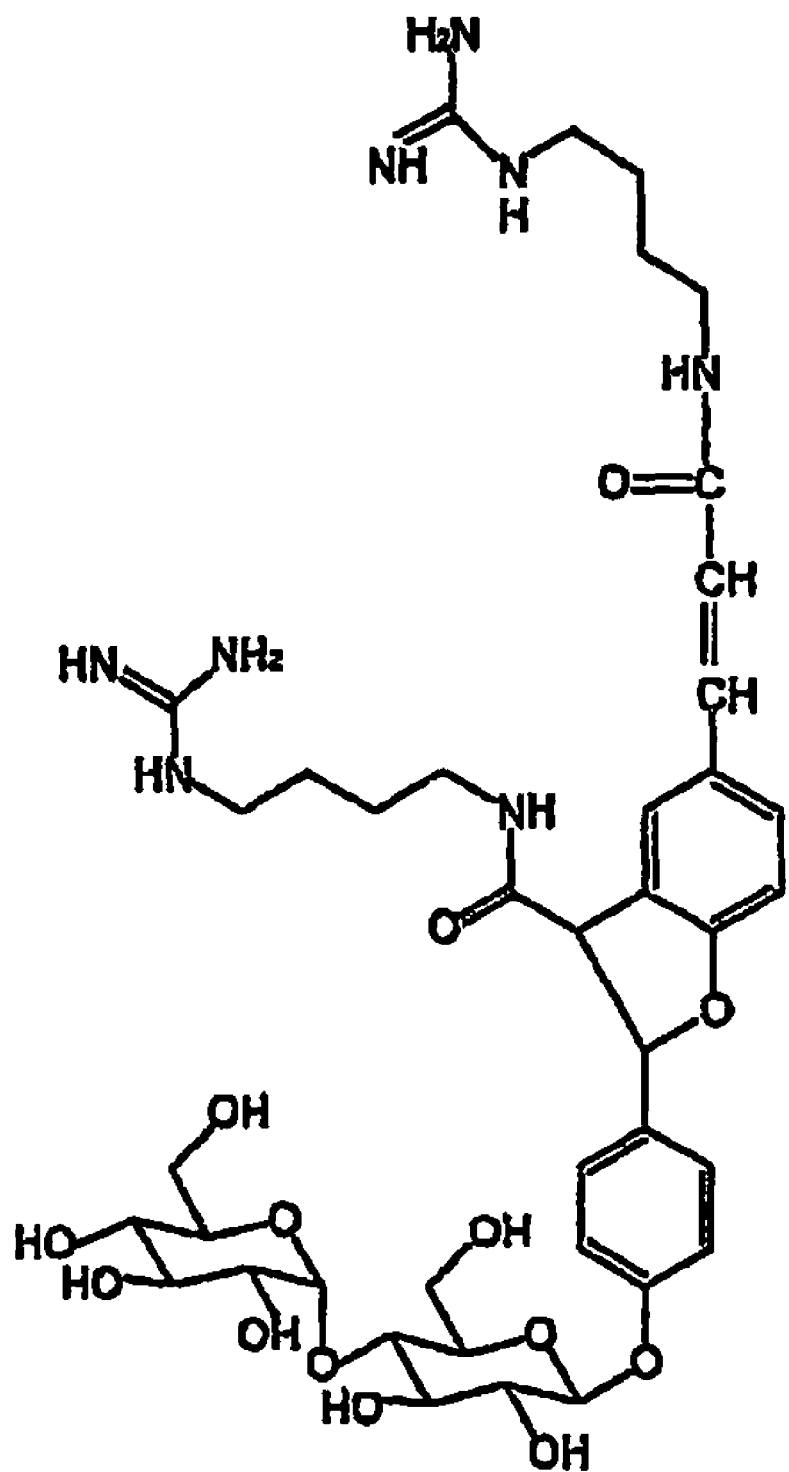
Figure 11:
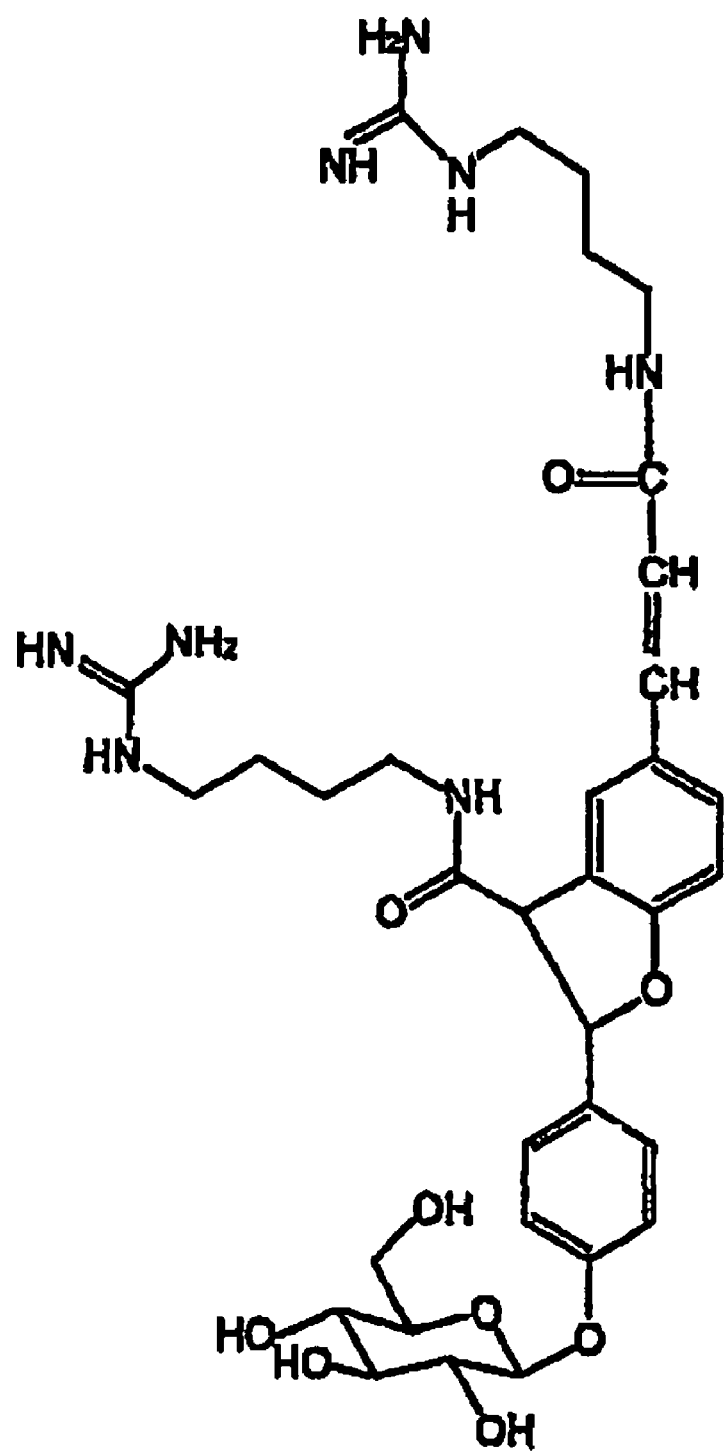
Figure 12:
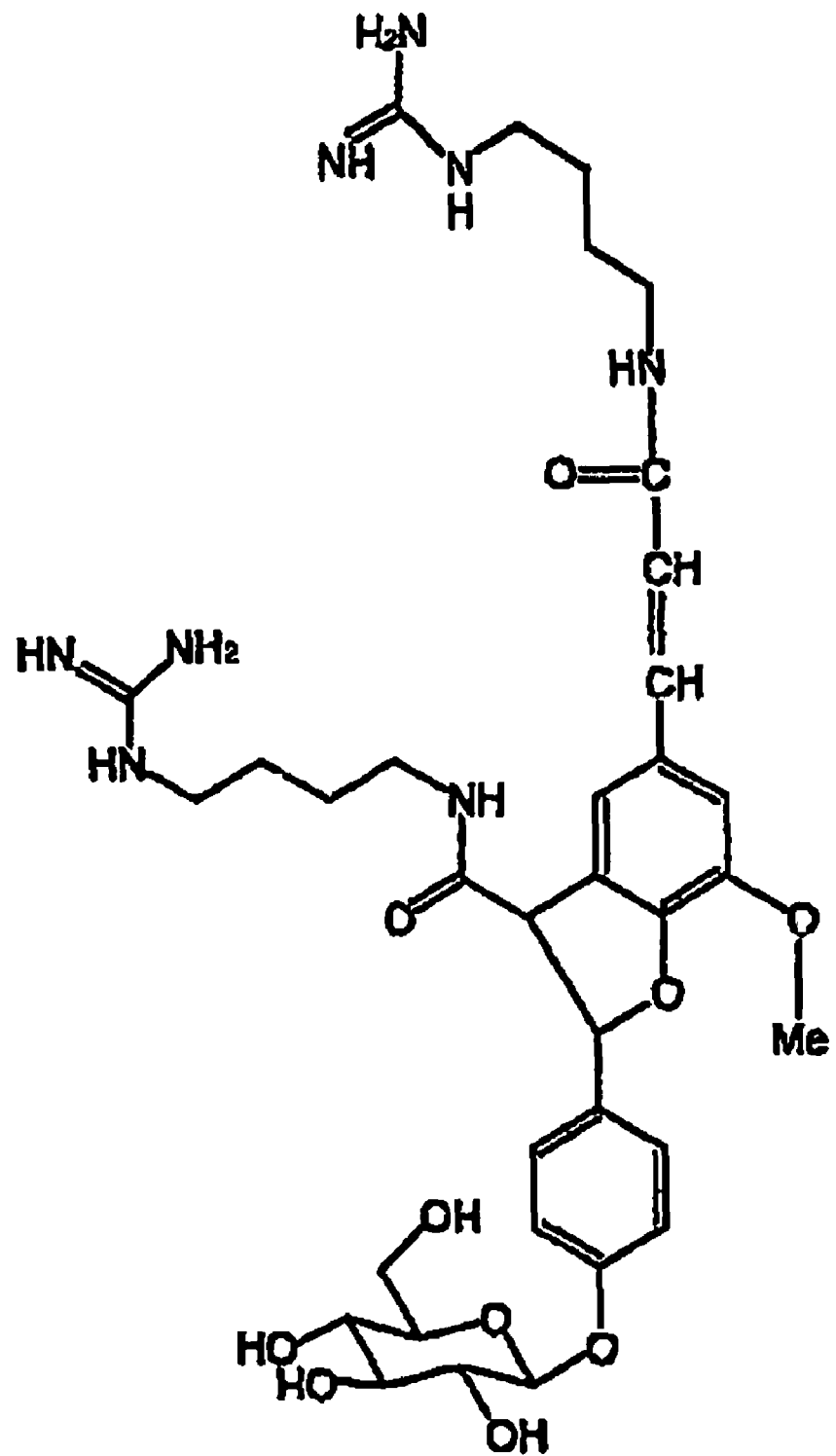

Separating and refining methods for oral cavity stimulating substances 1-3 which are the compounds of this invention and whose structural formulas are shown in FIGS. 10-12 will be mainly described hereinafter as embodiments of this invention.

Embodiment

Germinated grains that may contain the compounds (oral cavity stimulating substances 1-3) of this invention include, but are not limited to, for example, barley, wheat, rye, oats, oat wheat, adlay, rice, corn, Japanese millet, foxtail millet, broomcorn millet, buckwheat, soybean, red bean, pea, broad bean and butter bean.

The "germinated grains" in the embodiments include, besides whole germinated grams, fractions thereof (e.g. albumen, budlet, husk and so on), and products obtained by processing the germinated grains or their fractions. The processed products may be any objects as long as a certain process is applied to the germinated grains or their fractions, and include, but are not limited to, for example, milled objects, crushed objects, ground objects, dried objects, freeze-dried objects, and extracted (including supercritically extracted) objects, concentrates thereof, and solid contents after extraction.

Barley refers to plants of the genus barley, which include, but are not limited to, by scientific name, *Hordeum vulgare* L., *Hordeum distichon* L., and so on. In terms of cultivation, for example, they include spring barley and winter barley, and by species, two-row barley and six-row barley. Specific breeds include, for Japan, but are not limited to, Haruna two-row, Amagi two-row, Mikamo Golden, and Takaho Golden, and for abroad, but are not limited to, Alexis, Schooner, Harrington, Orbit, Corniche, and Triumph.

Germinated barley (malt) refers to grains of barley having grown or developed. In manufacture of malt, for example, it refers to green malt (raw malt) and dry malt. In cultivation of grains of barley, it refers to, but is not limited to, a state of young leaves and seedlings. The degree of germination of barley in manufacture of malt may be determined as appropriate by controlling factors such as temperature of barley in growth, moisture content supplied during germination, ratio of oxygen and carbon dioxide gas in sprout surface, and germination period. The moisture of green malt (raw malt) may be about 40 to 45%, and the moisture of dry malt about 3 to 15%.

The fractions of malt refer to, and are not limited to, tissue fractions such as husk, starch layer (albumen), pericarp and seed coat, leaf bud, young leaf, seedling, budlet, aleurone layer fraction, malt root and root bud, and mixtures thereof. Such fractions of germinated barley can be prepared by conventional methods, specific examples of which include the crushing method, screening method, milling method, wind selection method, specific gravity difference screening method, and threshing method.

Among these, budlets in particular can advantageously be used as raw materials including the compounds (oral cavity stimulating substances 1-3) of this invention.

As methods of acquiring the compounds (oral cavity stimulating substances 1-3) of this invention from such barley, malt or fractions of malt, compositions including these substances can be obtained through various extracting or separating operations by conventional methods. More particularly, extracting or separating processes that can be combined as appropriate include separation by distribution equilibrium such as solid-liquid extraction (water type extraction, organic solvent type extraction or the like), supercritical gas extraction, or adsorption (activated carbon or the like); separation based on velocity differential such as filtration, dialysis, membrane separation (ultrafiltration, RO, or functional film), liquid chromatography (reversed phase partition chromatography, normal phase partition chromatography, ion exchange chromatography, size exclusion chromatography or the like); and separation by formation of selective precipitation such, as crystallization, precipitation by an organic solvent, or the like.

If required, concentration, filtration and drying may be performed as appropriate to obtain the oral cavity stimulating substances of this invention in various forms such as concentrated extracts, fine particles, dried form, crystals and so on. The purity of such compositions is not limitative, but may be determined as appropriate according to the characteristics of foods and drinks to which they are applied, or additives (flavoring agents). Coarse refined products are acceptable, or they may be high-purity refined products. Refined products of high purity are required when the molecular weights, chemical constitutions and so on of the oral cavity stimulating substances of this invention are checked by MS spectrum analysis or NMR spectrum analysis using specially a precision analytical instrument. Then, a method may be used for repeating liquid chromatography until refined products of desired purity are obtained, by changing columns according to refining stages as necessary.

The foods and drinks herein refer to alcoholic beverages, nonalcoholic drinks and foods. The alcoholic beverages refer to liquids containing 0.1% or more of alcohol at 20° C., which include, but are not limited to, for example, malt fermented drinks such as beer and happoshu (low-malt beer), distilled liquors such as whiskey, spirits, and "shochu" of white liquor 1 and 2, blended liquor such as liqueur, zasshu (other miscellaneous liquors). Among these, malt fermented drinks are particularly suitable. The nonalcoholic drinks indicate soft drinks, tea drinks, carbonated drinks, milk beverages, coffee drinks, soy milk drinks and so on.

The foods refer to, but are not limited to, confectionery, boiled rice, noodles, agricultural foods (e.g. tofu, processed goods thereof), seasonings (sweet sake, vinegar, soy sauce, bean paste, dressing and so on), stock-breeding and dairy foods (yogurt, ham, bacon, sausage, mayonnaise and so on), and fish pastes (boiled fish paste, fish sausage and so on).

The compounds (oral cavity stimulating substances 1-3) of this invention separated and refined as described above can apply various oral cavity stimuli to foods and drinks according to concentrations thereof. The stimuli include, for example, acridness, bitterness, sweet taste, numb feeling, intake feeling and satisfaction at drinking, which act on the throat or the tongue. In particular, acridness has been confirmed over a wide range of concentrations.

By adding the compounds of this invention as an oral cavity stimulating agent (acridity applying agent) to food or drink, a flavor of oral cavity stimulus such as acridness is newly applied (or enhanced), the food or drink is given a flavor of increased depth and a satisfying quality of eating (or drinking). The acidity applying agent may be manufactured by using the compounds (oral cavity stimulating substances 1-3) of this invention alone, or in a desired combination by adjusting the blending quantity of each as appropriate. The form of the acridity applying agent may be, but are not limited to, dry products, liquid products or powder products. For example, freeze-dried products of oral cavity stimulating substances 1-3 separated and refined from raw materials, or the freeze-dried products having a suitable excipient added thereto, may be used advantageously. Alternatively, fractions of barley budlets containing a large quantity of oral cavity stimulating substance may be powdered, and an acridity applying agent may be made of this powder alone, or by adding a suitable excipient to the powder.

When adding the acridity applying agent to food or drink, the quantity of addition can be set as appropriate. No adding method is limitative. In the case of beer which is one of malt fermented drinks, for example, the agent may be added after fermentation, or may be added at any stage of the beer manufacturing process. It may be any stage, for example, a wort brewing step or a step of fermentation by yeast. The agent may be added just before the yeast filtration, a stage close to the finished product.

Other Embodiments

The oral cavity stimulating substances in this embodiment are separated and refined from germinated grains, but are not limited thereto. For example, they may be separated from other natural plants, or may be made artificially by organic synthesis.

Embodiment 1

Example of Manufacture of Happoshu (Low-Malt Beer)

A test was carried out to determine fractions containing large quantities of compounds (oral cavity stimulating substances 1-3) of this invention. Malt was fractionated, and only budlets were hand-picked by visual observation to be used as raw material.

22.0 kg of ground malt and 3.0 kg of budlets were mixed with 100 L of water, and a wort was manufactured in accordance with the conventional method. After filtering out malt lees, water was added to the wort obtained, to adjust it to a 14% stock wort extract. 22 L of the adjusted wort was mixed with 16.5 kg of saccharified starch, and water was added to obtain a total volume of 120 L. About 100 g of hop pellet was added to this, and it was boiled for about one hour. After cooling it to 13° C., water was added to adjust the stock wort extract concentration of the wort after the boiling to 14%, and about 300 g of yeast was added to allow fermentation for seven days to obtain happoshu (low-malt beer) (trial product 1). As a control, ordinary happoshu (low-malt beer) was manufactured without adding budlets (control product 1). An organoleptic evaluation was performed for both happoshu (low-malt beer).

The organoleptic evaluation employed a method in which ten panelists evaluated the degree of acridness by three-point full mark, and an average mark was calculated for each of trial product 1 and control product 1. The temperature of the samples was 5° C. The results are shown in Table 1. As shown in Table 1, trial product 1 had stronger acridness than control product 1. This confirms that budlets contain large amounts of acridity components.

TABLE 1

| | control product 1 | trial product 1 |
|---|---|---|
| organoleptic evaluation for acridness | 0.9 | 2.5 |

Embodiment 2

Isolation and Structural Analysis of Acrid Components

The following operation was carried out to fractionate malt and obtain budlet fractions having a large content of compounds (oral cavity stimulating substances 1-3) of this invention.

Of the malt noted above, only budlets hand-picked by visual observation were used as starting material. Subsequently, as shown in FIG. 1, 40 g of the budlets obtained were dissolved in 160 mL of water, and maintained at 65° C. for 30 minutes. The extract was put to centrifugal separation, and the supernatant liquid was applied to Sep-Pac C18 Resin (Sep-Pak Vac 20 cc C18 Cartridge manufactured by Waters), and was eluted, respectively, in 20 mL of water, 20 mL of 20% ethanol, 20 mL of 50% ethanol, and 20 mL of 100% ethanol. Each eluted fraction was condensed using an evaporator, and freeze-dried, to obtain coarse fractionation powder. It has been found by flavor evaluation, that acrid components are present in the 20% ethanol eluted fraction.

The 20% ethanol eluted fraction (dry weight at 90.4 mg) was fractionated again as coarse fractionated acrid component using HPLC System manufactured by Gilson. The column used was Deverosil-C30-UG5 (10×250 mm: manufactured by Nomura Chemicals), and analytic conditions were that solution A was an aqueous solution of 0.05% TFA (trifluoroacetic acid), and solution B was a 90% acetonitrile solution of 0.05% TFA. A linear gradient was set for 150 minutes from 0% to 50% of solution B at a flow rate of 3 mL/min. Detection was carried out by UV absorption with a wavelength of 300 nm. Each peak was isolated, and flavor evaluation is performed for each peak, to determine components with strong and sharp acridness and obtain acrid component powder (dry weight at 61.2 mg).

Figure 2:
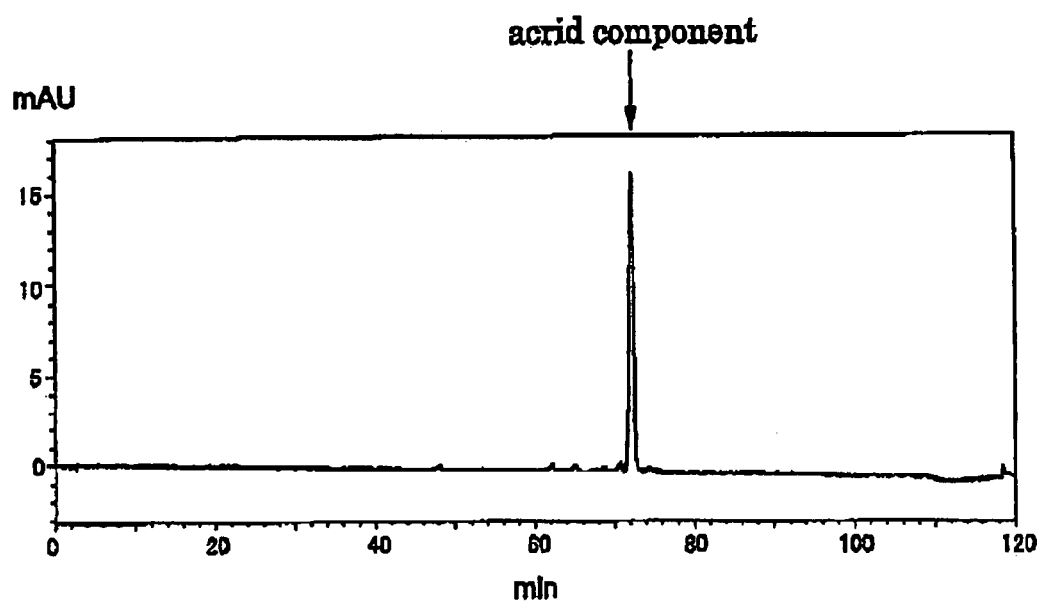

This acrid component powder was put to HPLC again for the purpose of refining. The analysis was conducted with HPLC System CLASS-VP Series (manufactured by Shimadzu Corp.). The column used was Deverosil-C30-UG5 (4.6×150 mm: manufactured by Nomura Chemicals), and analytic conditions were that solution A was an aqueous solution of 0.05% TFA (trifluoroacetic acid), and solution B was a 90% acetonitrile solution of 0.05% TFA. A linear gradient was set for 100 minutes from 0% to 20% of solution B at a flow rate of 1 mL/min. Detection was carried out by UV absorption with a wavelength of 300 nm. This chromatogram is shown in FIG. 2. The peak was about one. It has also been confirmed by flavor evaluation that concentration of the acrid component was proportional to the strength of acridness.

The peak concerned was isolated, and an instrumental analysis was conducted preparatorily. It was found that the acrid component was a mixture of a plurality of substances. Then, the peak concerned was further isolated by the following method.

It was separated with HPLC System CLASS-VP Series (manufactured by Shimadzu Corp.) using Capcellpak-MF-C1 (4.6×150 mm: manufactured by Shiseido Co.) column. Analytic conditions were isocratic with an aqueous solution of 0.05% TFA at a flow rate of 1 mL/min. Detection was carried out by UV absorption with a wavelength of 300 nm. The result is shown in FIG. 3.

Figure 3:
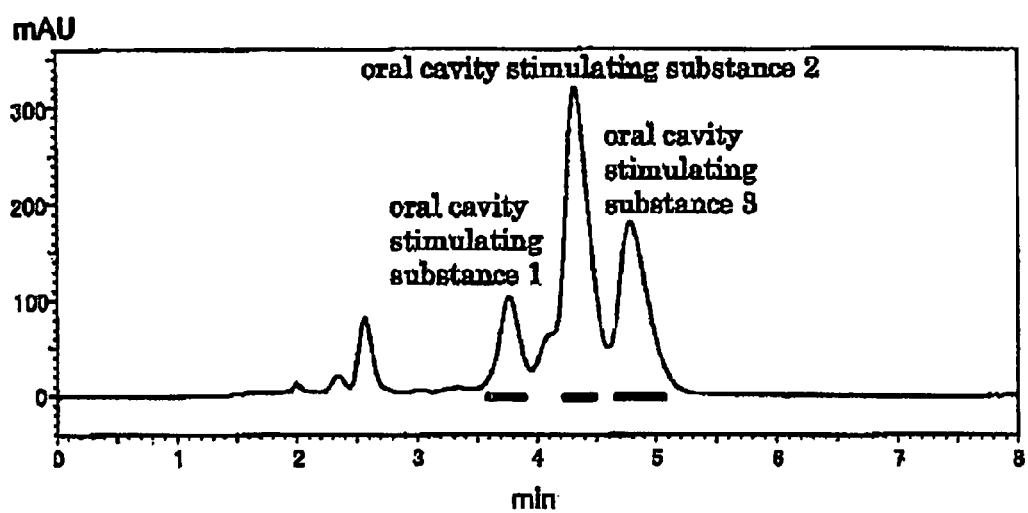

Each peak shown in FIG. 3 was isolated, and flavor was evaluated for each. Acridness was felt for the three underlined peaks, and these were named oral cavity stimulating substance 1, oral cavity stimulating substance 2 and oral cavity stimulating substance 3 (dry weight B were is 6.1 mg, 21.3 mg and 10.2 mg, respectively). Ten panelists evaluated the degree of acridness by three-point full mark, and an average mark was compared with the acrid component before refining. At this time, the degree of acridness the acrid component was set to 1 to serve as reference (see Table 2).

TABLE 2

|  | degree of acridness | impression |
|---|---|---|
| acrid component | 1 | strong stimulus, aftertaste remaining on tongue |

TABLE 2-continued

|  | degree of acridness | impression |
|---|---|---|
| oral cavity stimulating substance 1 | 1.7 | strong acridness, aftertaste, stimulating |
| oral cavity stimulating substance 2 | 0.9 | strong stimulus, aftertaste remaining on tongue |
| oral cavity stimulating substance 3 | 1.2 | strong acridness, slightly sweet |

Figure 4:
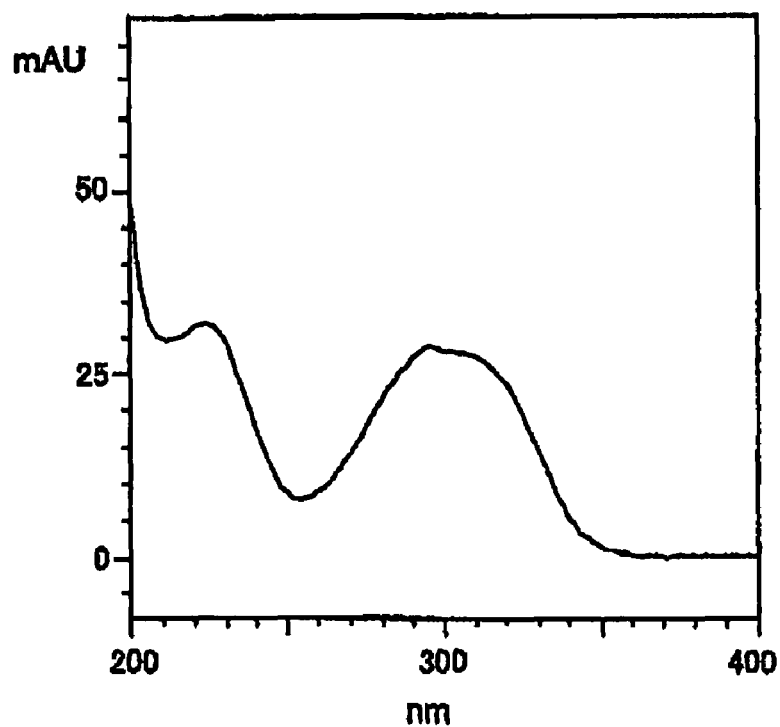
Figure 5:
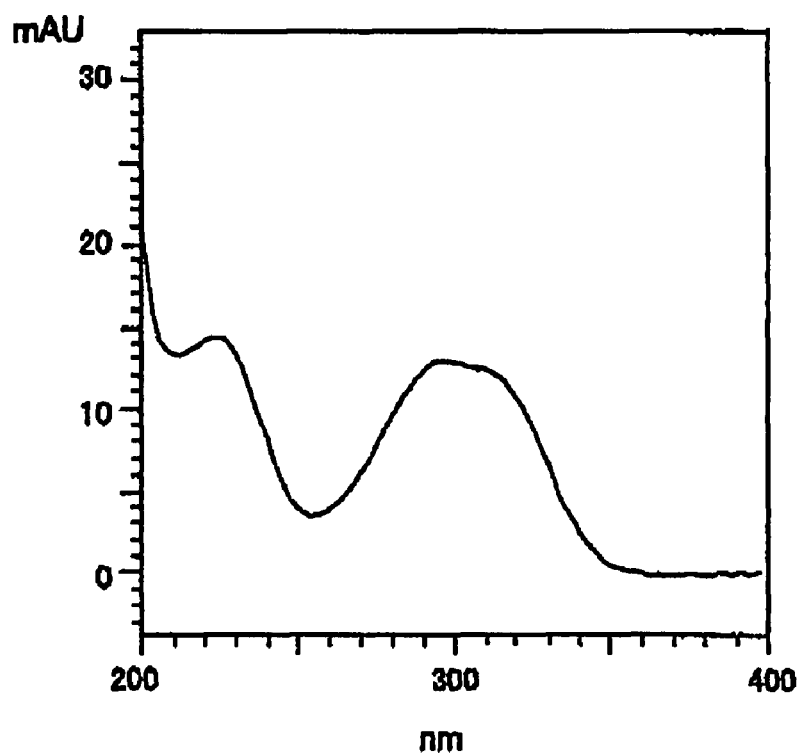
Figure 6:
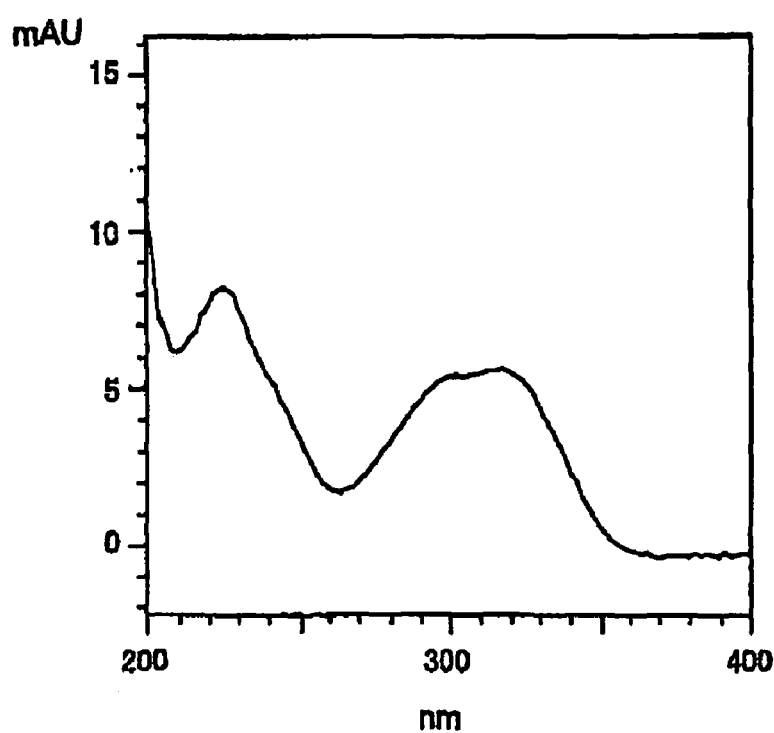

Chemical structures of these oral cavity stimulating substance 1, oral cavity stimulating substance 2 and oral cavity stimulating substance 3 were determined with UV absorption spectra, mass spectrometry and NMR analysis. The UV absorption spectra are shown in FIGS. 4, 5 and 6, respectively, the results of the mass analysis in the following table 3, and proton NMR spectra in heavy methanol in FIGS. 7, 8 and 9.

TABLE 3

Results of high resolution mass spectrometry by FAB ionization (cationization)

| | Scan | | | |
|---|---|---|---|---|
| | (5, 7) | (8, 10) | (11, 13) | (14, 16) |
| oral cavity stimulating substance 1 | | | | |
| Observed m/z | 875.4132 | 875.4143 | 875.4150 | 875.4159 |
| Int % | 100 | 100 | 100 | 100 |
| oral cavity stimulating substance 2 | | | | |
| Observed m/z | 713.3595 | 713.3604 | 713.3621 | 713.3618 |
| Int % | 100 | 100 | 100 | 100 |
| oral cavity stimulating substance 3 | | | | |
| Observed m/z | 743.3746 | 743.3729 | 743.3754 | 743.3754 |
| Int % | 29.2 | 32.6 | 31.0 | 33.0 |

From these analytical information, the structures of oral cavity stimulating substance 1, oral cavity stimulating substance 2 and oral cavity stimulating substance 3 were determined. Respective structural formulae are shown in FIGS. 10-12.

Regarding oral cavity stimulating substance 1, —CH=CH— in FIG. 10 was cis or trans. In this refining process, it was a mixture thereof.

Regarding oral cavity stimulating substance 2, —CH=CH— in FIG. 11 was trans. Similar oral cavity stimulating action is expected of cis.

Regarding oral cavity stimulating substance 3, —CH=CH— in FIG. 12 was cis or trans. In this refining process, it was a mixture thereof.

Embodiment 3

Examples are shown in which the compounds (oral cavity stimulating substances 1-3) of this invention were added to beer products. Each of oral cavity stimulating substance 1, oral cavity stimulating substance 2 and oral cavity stimulating substance 3 obtained in Embodiment 2 were added to 100% malt beer, and organoleptic evaluation was carried out.

To 100 mL of beer made by using 100% of usual two-row malt from Europe (content of oral cavity stimulating substance 1: 1.4 ppm, content of oral cavity stimulating substance 2: 5.7 ppm, and content of oral cavity stimulating substance 3: 2.7 ppm), 1 mg of oral cavity stimulating substance 1 obtained in Embodiment 1 was added to obtain trial product 2, 1 mg of oral cavity stimulating substances 2 was added to obtain trial product 3, and 1 mg of oral cavity stimulating substances 3 was added to obtain trial product 4. Organoleptic evaluation was carried out by the same method as in Embodiment 1. The concentrations of oral cavity stimulating substances 1-3 were measured by the method of Embodiment 7 described hereinafter.

The results of organoleptic evaluation of the beers added are shown in Table 4.

TABLE 4

|  | control product 2 100% malt beer | trial product 2 oral cavity stimulating substance 1 added | trial product 3 oral cavity stimulating substance 2 added | trial product 4 oral cavity stimulating substance 3 added |
|---|---|---|---|---|
| oral cavity stimulating substance 1 | 1.4 | 11.4 | 1.4 | 1.4 |
| oral cavity stimulating substance 2 | 5.7 | 5.7 | 15.7 | 5.7 |
| oral cavity stimulating substance 3 | 2.8 | 2.8 | 2.8 | 12.8 |
| total oral cavity stimulating substances | 9.9 | 19.9 | 19.9 | 19.9 |
| organoleptic evaluation of acridness | 1.4 | 2.4 | 1.8 | 2.0 |

*The numbers other than the results of organoleptic evaluation are concentrations of the oral cavity stimulating substances (ppm).

Table 4 shows the beers with each of oral cavity stimulating substance 1, oral cavity stimulating substance 2 and oral cavity stimulating substance 3 added have higher degrees of acridness than with the ordinary beer serving as the control product. Thus, it has been confirmed that acridness is given by the compounds (oral cavity stimulating substances 1-3) of this invention.

Embodiment 4

Example of Manufacture of Acridity Adding Agents

Acrid components were refined from malt to obtain acridity adding agents. Acrid component powder was manufactured based on the method described in Embodiment 2. 1 kg of budlets was extracted with 4 L of warm water at 65° C. for 30 minutes. After putting the extract to centrifugal separation, 1 kg of Cosmo Seal 75C18-OPN Resin (manufactured by Nakarai Tesuku) was added to the supernatant, which was agitated for 30 minutes. Subsequently, the supernatant was discarded, and resin adsorption fractions were eluted in 1 L of 20% ethanol. After condensing the eluate with an evaporator, the eluate was fractionated using HPLC System manufactured by Gilson. The column used was Deverosil-C30-UG5 (20×250 mm: manufactured by Nomura Chemicals), and analytic conditions were that solution A was an aqueous solution of 0.05% TFA (trifluroacetic acid), and solution B was a 90% acetonitrile solution of 0.05% TFA. A linear gradient was set for 150 minutes from 0% to 40% of solution B at a flow rate of 5 mL/min. Detection was carried out by UV absorption with a wavelength of 300 nm. The peaks of acrid components identified in Embodiment 1 were isolated. This was repeated, and after condensing with an evaporator, freeze-drying was carried out to obtain 1.5 g of acrid component powder (acridity adding agent 1). 1.2 g of acridity adding agent 1 obtained by the same method was added to and mixed with 1.2 kg of cornstarch. The mixture obtained presented strong acridity (acridity adding agent 2).

Embodiment 5

Example of Manufacture of Happoshu (Low-Malt Beer) with Acridity Adding Agent 1 Added Thereto Acridity adding agent 1 obtained in Embodiment 4 was added to happoshu (low-malt beer) obtained by conventional method, to prepare happoshu (low-malt beer) with enhanced acridness. 2 mg, 4 mg, 8 mg and 16 mg of acrid component powder were added to 500 mL of ordinary happoshu (low-malt beer) to make trial product 5, trial product 6, trial product 7 and trial product 8 of happoshu (low-malt beer), respectively. Table 5 shows results of organoleptic evaluation carried out by the method of Embodiment 1. Happoshu (low-malt beer) with no acrid component added was also evaluated as control (control product 3).

TABLE 5

|  | Acrid component concentration (ppm) | organoleptic evaluation |
|---|---|---|
| control product 3 | 5.1 | 0.7 |
| trial product 5 | 7.2 | 1 |
| trial product 6 | 10.4 | 1.1 |
| trial product 7 | 13.2 | 1.8 |
| trial product 8 | 22.4 | 2.4 |

A correlation has been found from Table 5 between concentration of the acrid component and the results of organoleptic evaluation of acridness of the happoshu (low-malt beer) made as trail. This shows that happoshu (low-malt beer) of various degrees of acridness can be prepared by using the acridity adding agent of this invention.

Embodiment 6

Example of Manufacture of Happoshu (Low-Malt Beer) with Acridity Adding Agent 2 Added Thereto Happoshu (low-malt beer) was manufactured by using acridity adding agent 2 obtained in Embodiment 4. 6.0 kg of ground malt, 1.2 kg of acridity adding agent 2 obtained in Embodiment 3 and 30 L of water were mixed, and a wort was manufactured in accordance with the conventional method. After filtering out malt lees, saccharified starch was added to the wort obtained to make the ratio of malt used 24%, and water was added to adjust it to a 14% stock wort extract concentration. About 100 g of hop pellet was added to this, and it was boiled for about one hour. After cooling it to 13° C., about 300 g of yeast was added to allow fermentation for seven days to obtain happoshu (low-malt beer) (trial product 8). Table 6 shows results of organoleptic evaluation carried out in comparison with ordinary happoshu (low-malt beer) serving as control. It has been found that happoshu (low-malt beer) with various degrees of acridness can be prepared by using the acridity adding agent of this invention.

TABLE 6

|  | control product | trial product 8 |
| --- | --- | --- |
| organoleptic evaluation for acridness | 0.9 | 1.9 |

Embodiment 7

Method of Analyzing Oral Cavity Stimulating Substances 1-3

An example of analyzing oral cavity stimulating substances 1-3 in a first wort in the beer manufacturing process will be shown.

30 kg of two-row barley malt from Europe was mixed with 120 L of water, saccharified at 65° C. for 60 minutes, and put to Reuter filtration, to obtain a first wort adjusted to 14% stock wort extract.

Figure 13:
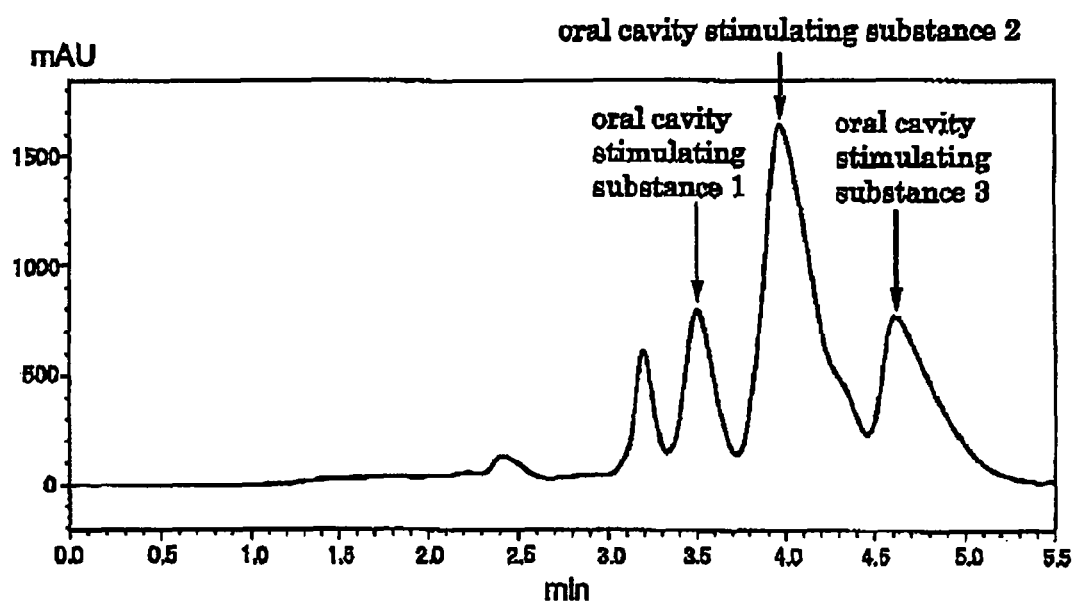

20 g of the above first wort was applied to Sep-Pac C18 Resin (Sep-Pak Vac 20 cc C18 Cartridge manufactured by Waters), and after cleaning successively with 20 mL of water and 7% ethanol, fractions eluted in 20 mL of 15% ethanol were condensed using an evaporator, and put to HPLC analysis. The analysis was performed with HPLC System CLASS-VP Series (manufactured by Shimadzu Corp.) using Capcellpak-MF-C1 (4.6×150 mm: manufactured by Shiseido Co.) column. Analytic conditions were isocratic with an aqueous solution of 0.05% TFA at a flow rate of 1 mL/min. Detection was carried out by UV absorption with a wavelength of 300 nm. The chromatogram is shown in FIG. 13.

An analytical curve was created using oral cavity stimulating substances 1-3 obtained in Embodiment 2 as standard substances, and each was able to be quantified. By this method, each of oral cavity stimulating substances 1-3 contained in liquors and food and drink such as a wort, and half-finished products thereof was quantitatively analyzed.

Embodiment 8

Method of Analyzing Acrid Component

Figure 14:
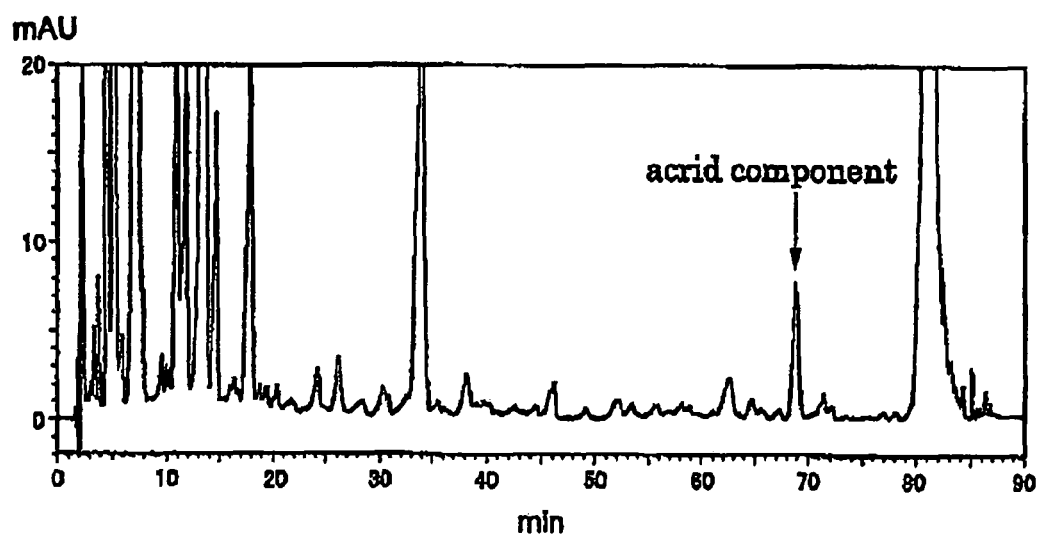

An example of analyzing acrid component in a first wort in the beer manufacturing process will be shown. 30 kg of two-row malt from Europe was mixed with 120 L of water, saccharified at 65° C. for 60 minutes, and put to Reuter filtration, to obtain a first wort adjusted to 14% stock wort extract. 1 mL of the first wort was pawed through a filter of 0.45 μm pore size manufactured by Millipore, and 10 μL was put to HPLC analysis. The analysis was performed with HPLC System CLASS-VP Series (manufactured by Shimadzu Corp.) using Deverosil-C30-UG5 (4.6×150 mm: manufactured by Nomura Chemicals) column. Analytic conditions were that solution A was an aqueous solution of 0.05% TFA (trifluoroacetic acid), and solution B was a 90% acetonitrile solution of 0.05% TFA. A linear gradient was set for 100 minutes from 0% to 20% of solution B at a flow rate of 1.0 mL/min. Detection was carried out by UV absorption with a wavelength of 300 nm. This chromatogram is shown in FIG. 14.

An analytical curve was created using acridity adding agent 1 obtained in Embodiment 4 as standard substance, and quantity was determined. By this method, acrid components contained in liquors and food and drink such as a wort and half-finished products thereof were analyzed easily, and the degree of acridness was measured quickly.

Embodiment 9

High Precision Simple Analysis Method of Oral Cavity Stimulating Substance

A method of simply and precisely analyzing concentration of only oral cavity stimulating substance 2 will be shown.

This method uses high performance liquid chromatography (HPLC) to separate the objective component roughly by a one-dimensional column, to heart cut fractions including the objective component by column switching and put them to a two-dimensional column, and to analyze with sufficient precision at the two-dimensional stage. An example in which the acridness component of beer was measured using this method will be shown.

Figure 15:
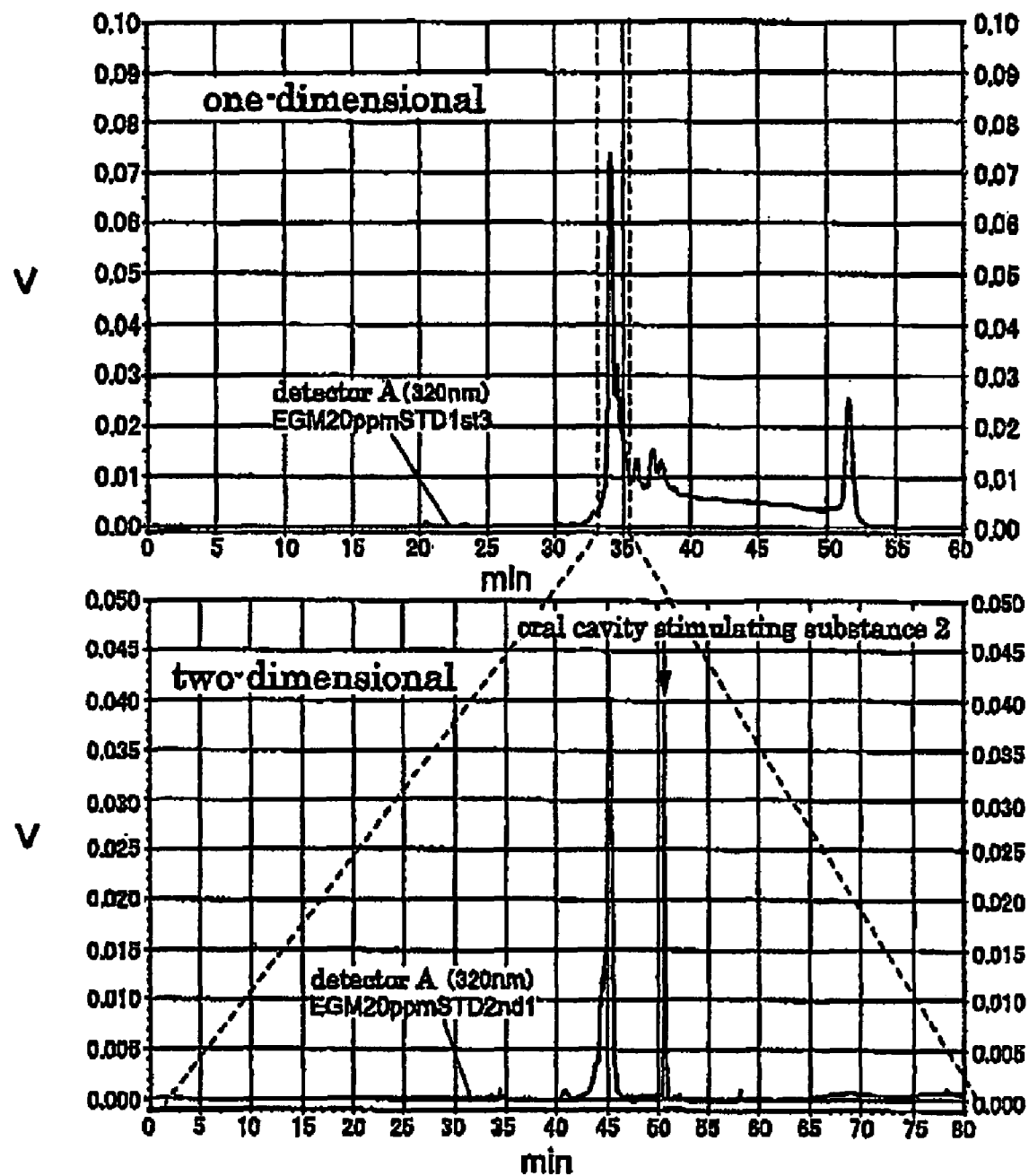

5 mL of beer was passed through a filter of 0.45 μm pore size manufactured by Millipore, and analyzed using HPLC System CLASS-VP Series (manufactured by Shimadzu Corp.). For the one-dimensional and two-dimensional, pre-concentration column [PVA (4 mm×30 mm), SCR-RP3, #228-33713-91, manufactured by Shimadzu] was connected before a separating column. An injection quantity for the one-dimensional was 100 μL, and separation was carried out using Deverosil-C30-UG5 (4.6×150 mm, manufactured by Nomura chemicals) column. Analytical conditions were that solution A was an aqueous solution of 0.05% TFA, and solution B was a 90% 0.05% TFA, 50% MeOH. A gradient was 0% (0 min.)-20% (25 min.)-80% (40 min.)-0% (50 min.) of solution B % at a flow rate of 0.6 mL/min. Detection was carried out by UV absorption with a wavelength of 320 nm. The fractions eluted from 34 minutes to 35 minutes for the second-dimensional were heart cut, and put to an analysis of the two-dimensional. Separation of the two-dimensional was carried out by connecting three symmetry-C18ODS (4.6×150 mm, 3.5 μm, manufactured by Waters) columns in series. Analytical conditions were solution C: 0/5% TFA, 2% MeCN, and solution D: 0.05% TFA and 80% MeCN. A gradient was 20% (0 min.)-20% (37 min.)-60% (70 min.) of solution D at a flow rate of 0.6 mL/Min. Detection was carried out by UV absorption with a wavelength of 320 nm. A chromatogram is shown in FIG. 15. It has been confirmed separately that the peak in FIG. 15 was oral cavity stimulating substance 2 by a method of dissolving and introducing a proper quantity of oral cavity stimulating substance 2 in a sample solution.

An analytical curve was created using oral cavity stimulating substance 2 obtained in Embodiment 2 as standard substance, and the concentration of oral cavity stimulating substance 2 in the beer was measured. By this method, the acridness component of the beer was performed simply and with increased precision.

Embodiment 10

Acrid Component Analysis of Sprouted Grain

The acrid component was analyzed using sprouted brown, rice as one of sprouted grains.

Figure 16:
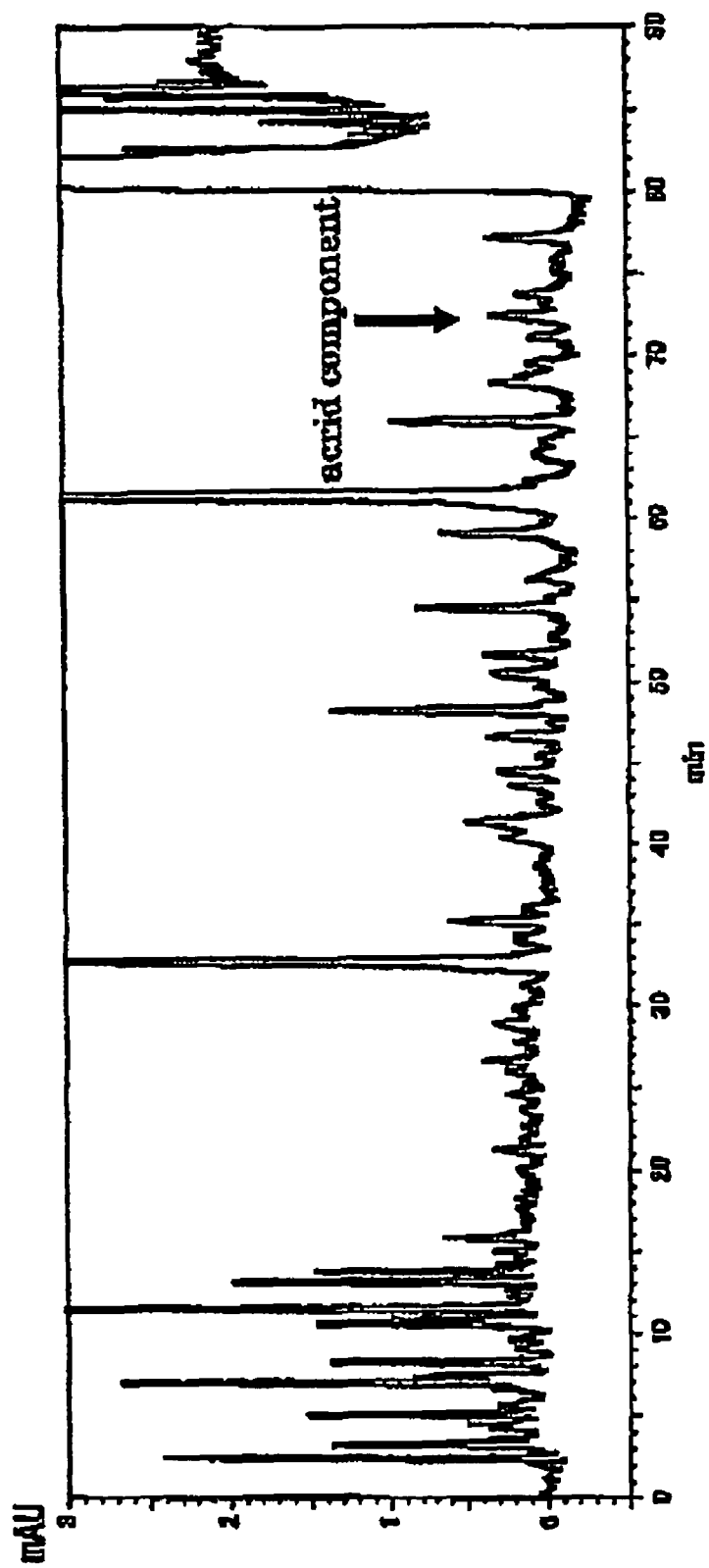

Sprouted brown rice from Nagano Pref. was ground with a commercially available small mill, 100 g of water was added to 25 g of the ground material, and it was processed at 65√ C. for 30 minutes. The processed liquid was put to a centrifugal separator (7000 rpm, 10 minutes, and 4° C.). In accordance with the method described in Embodiment 8, the acrid component contained in the supernatant liquid after centrifugal separation was analyzed. A chromatogram is shown in FIG. 16. The result of having created an analytical curve and determined quantity, it has been found that the content of the acrid component of the sprout brown rice is 2.4 μg/g.

Embodiment 11

Examples of Manufacture of Various Foods and Drinks Containing Acrid Components

Various foods and drinks containing acrid components were manufactured with the following compositions:

| (composition) | (parts by weight) |
|---|---|
| toffee: | |
| powder sorbitol | 99.7 |
| flavor | 0.2 |
| acrid component powder | 0.05 |
| sorbitol seed | 0.05 |
| sum | 100.00 |
| candy: | |
| sugar | 47.0 |
| starch syrup | 49.76 |
| flavor | 1.0 |
| water | 2.0 |
| acrid component powder | 0.24 |
| sum | 100.00 |
| troche: | |
| gum arabic | 6.0 |
| grape sugar | 73.0 |
| acrid component powder | 0.05 |
| potassium hydrogen phosphate | 0.2 |
| potassium dihydrogen phosphate | 0.1 |
| lactose | 17.0 |
| flavor | 0.1 |
| magnesium stearate | 3.55 |
| sum | 100.00 |
| gum: | |
| gum base | 20.0 |
| calcium carbonate | 2.0 |
| stevioside | 0.1 |
| acrid component powder | 0.05 |
| lactose | 76.85 |
| flavor | 1.0 |
| sum | 100.00 |
| caramel: | |
| granulated sugar | 32.0 |
| starch syrup | 20.0 |
| dried milk | 40.0 |
| hardened oil | 4.0 |
| salt | 0.6 |
| flavor | 0.02 |
| water | 3.22 |
| acrid component powder | 0.16 |
| sum | 100.00 |
| jelly (coffee jelly): | |
| granulated sugar | 15.0 |
| gelatin | 1.0 |
| coffee extract | 5.0 |
| water | 78.93 |
| acrid component powder | 0.07 |
| sum | 100.00 |
| ice cream: | |
| whipped cream (45% fat) | 33.8 |
| skim milk powder | 11.0 |

-continued

| (composition) | (parts by weight) |
|---|---|
| granulated sugar | 14.8 |
| sweetened egg yolk | 0.3 |
| vanilla essence | 0.1 |
| water | 39.93 |
| acrid component powder | 0.07 |
| sum | 100.00 |
| custard pudding: | |
| cows milk | 47.51 |
| whole egg | 31.9 |
| highly refined sugar | 17.1 |
| water | 3.4 |
| acrid component powder | 0.09 |
| sum | 100.00 |
| sweet jellied bean paste: | |
| red adzuki bean jam | 24.8 |
| carragheenan | 0.3 |
| salt | 0.1 |
| highly refined sugar | 24.9 |
| acrid component powder | 0.1 |
| water | 49.8 |
| sum | 100.0 |
| juice: | |
| frozen concentration Satsuma mandarin juice | 5.0 |
| fruit sugar grape sugar liquid sugar | 11.0 |
| citric acid | 0.2 |
| L ascorbic acid | 0.02 |
| acrid component powder | 0.05 |
| flavor | 0.2 |
| coloring matter | 0.1 |
| water | 83.43 |
| sum | 100.00 |
| carbonated drink: | |
| granulated sugar | 8.0 |
| concentration lemon juice | 1.0 |
| L ascorbic acid | 0.10 |
| citric acid | 0.09 |
| sodium citrate | 0.05 |
| coloring agent | 0.05 |
| flavor | 0.15 |
| aerated water | 90.55 |
| acrid component powder | 0.01 |
| sum | 100.00 |
| lactic acid bacteria beverage: | |
| 21% milk solid content fermented milk | 14.76 |
| fruit sugar grape sugar liquid sugar | 13.31 |
| pectin | 0.5 |
| citric add | 0.08 |
| flavor | 0.15 |
| water | 71.14 |
| acrid component powder | 0.06 |
| sum | 100.00 |
| coffee drink: | |
| granulated sugar | 8.0 |
| skim milk | 5.0 |
| caramel | 0.2 |
| coffee extract | 2.0 |
| flavor | 0.1 |
| polyglycerine fatty acid ester | 0.05 |
| salt | 0.05 |
| water | 84.56 |
| acrid component powder | 0.04 |
| sum | 100.00 |

| (composition) | (parts by weight) |
|---|---|
| fruit juice containing alcoholic beverage: | |
| 50 vol. % ethanol | 32.0 |
| sugar | 8.4 |
| fruit juice | 2.4 |
| acrid component powder | 0.2 |
| purified water | 57.0 |
| sum | 100.0 |
| tea drink: | |
| green tea extract | 2.0 |
| water | 97.4 |
| acrid component powder | 0.05 |
| vitamin C | 0.01 |
| sum | 100.0 |

INDUSTRIAL UTILITY

This invention is useful particularly in the manufacturing industry of liquor and food which uses sprouted grain (malt etc.) as raw material, and can contribute to further development of such industry.

BRIEF DESCRIPTION OP THE DRAWINGS

Figure 7:
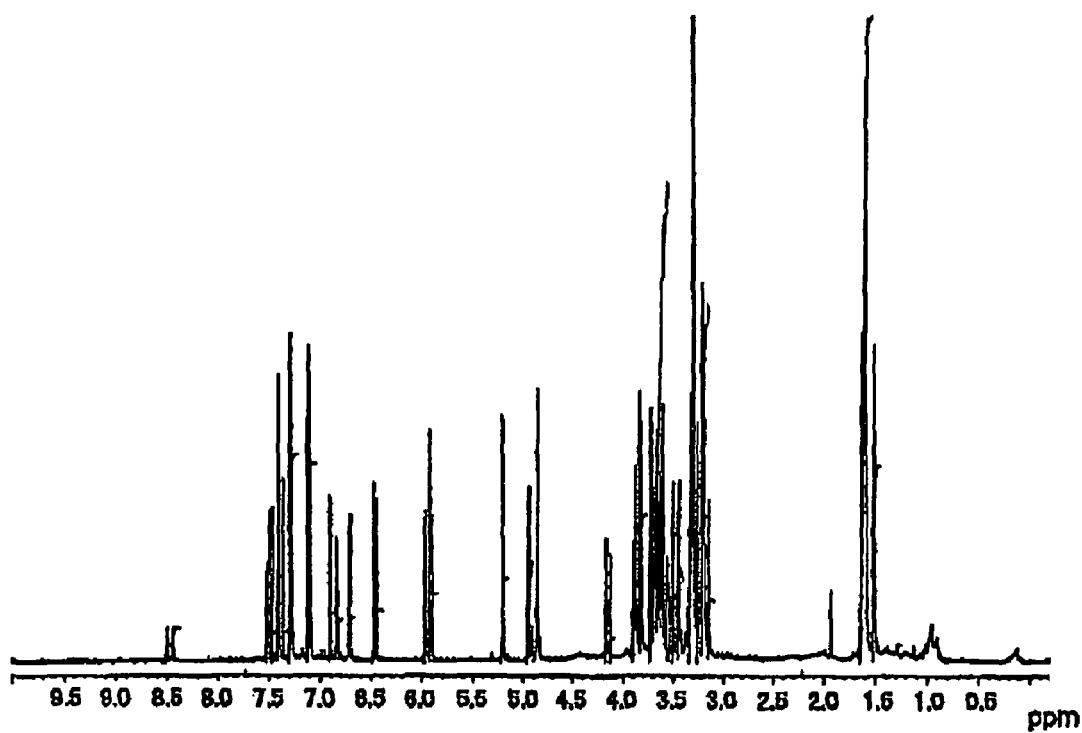
Figure 8:
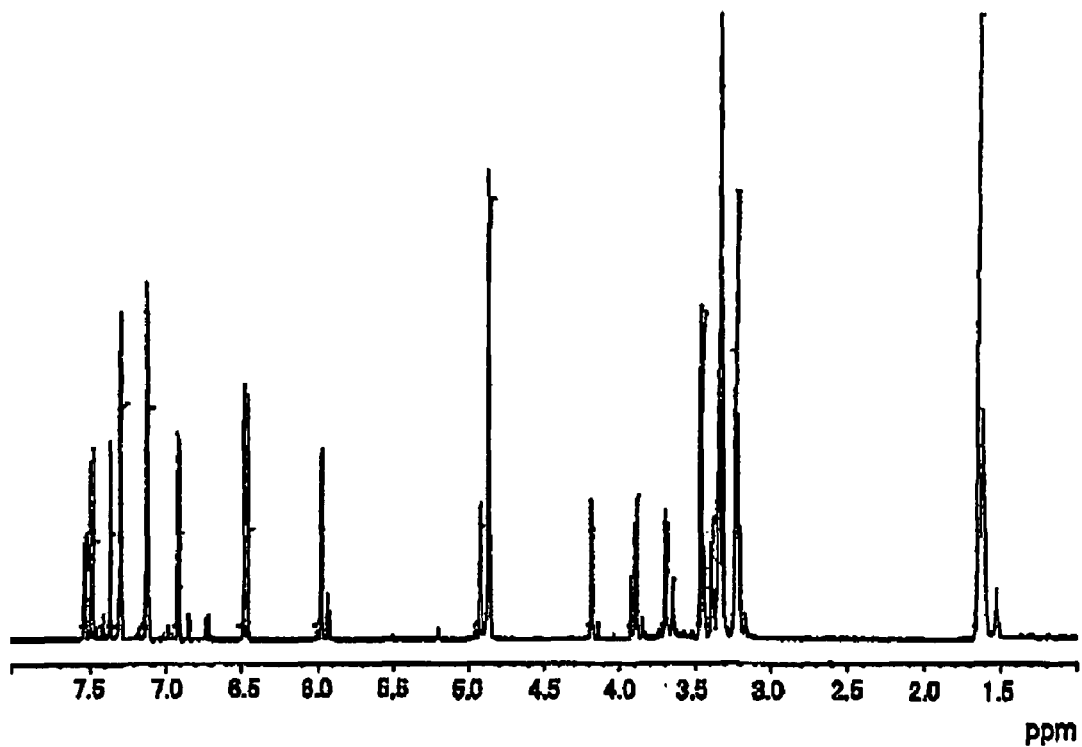
Figure 9:
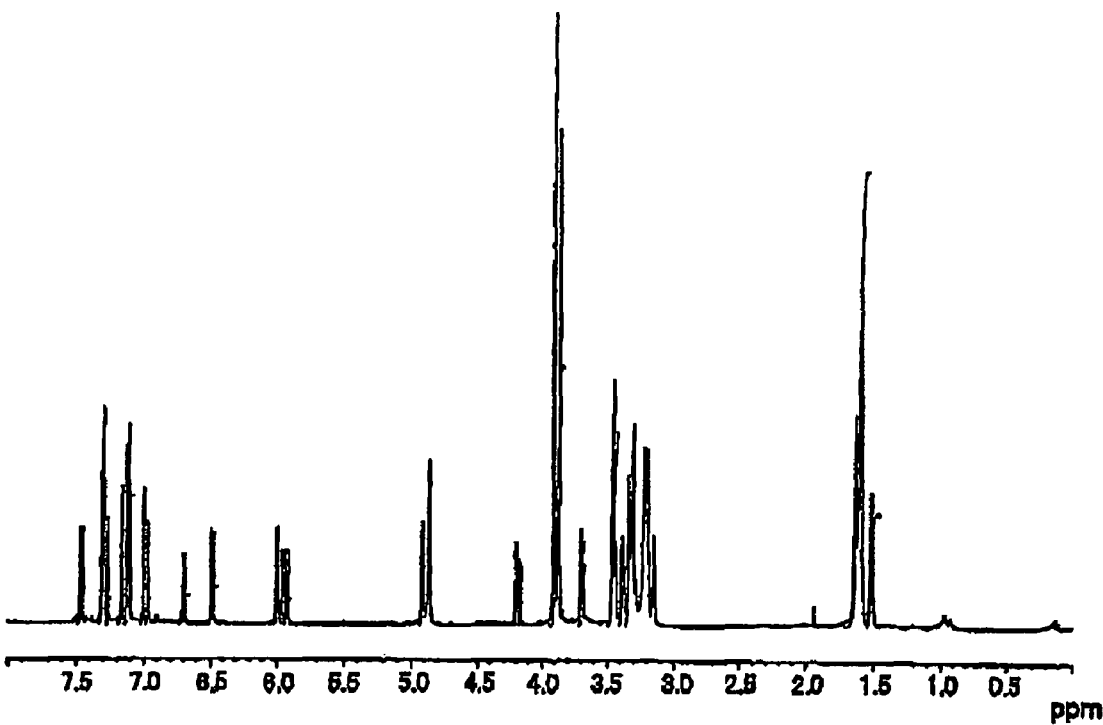

[FIG. 1]
Flow chart showing a process of refining oral cavity stimulating substances
[FIG. 2]
Chromatogram of an acrid component
[FIG. 3]
Chromatogram of oral cavity stimulating substances 1-3
[FIG. 4]
UV absorption spectrum of oral cavity stimulating substance 1
[FIG. 5]
UV absorption spectrum of oral cavity stimulating substance 2
[FIG. 6]
UV absorption spectrum of oral cavity stimulating substance 3
[FIG. 7]
Proton NMR spectrum of oral cavity stimulating substance 1
[FIG. 8]
Proton NMR spectrum of oral cavity stimulating substance 2
[FIG. 9]
Proton NMR spectrum of oral cavity stimulating substance 3
[FIG. 10]
Structural formula of oral cavity stimulating substance 1
[FIG. 11]
Structural formula of oral cavity stimulating substance 2
[FIG. 12]
Structural formula of oral cavity stimulating substance 3
[FIG. 13]
Analytical chromatogram of oral cavity stimulating substances 1-3 of wort
[FIG. 14]
Analytical chromatogram of acrid components of wort
[FIG. 15]
High precision analytical chromatogram of oral cavity stimulating substance 2 of beer
[FIG. 16]
Analytical chromatogram of acrid components of sprouted brown rice extract

The invention claimed is:

1. A compound of the following structural formula (I)

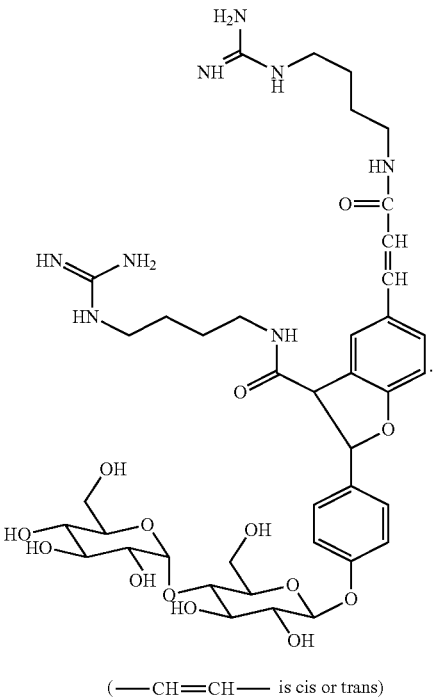

(—CH=CH— is cis or trans)

2. A compound of the following structural formula (II)

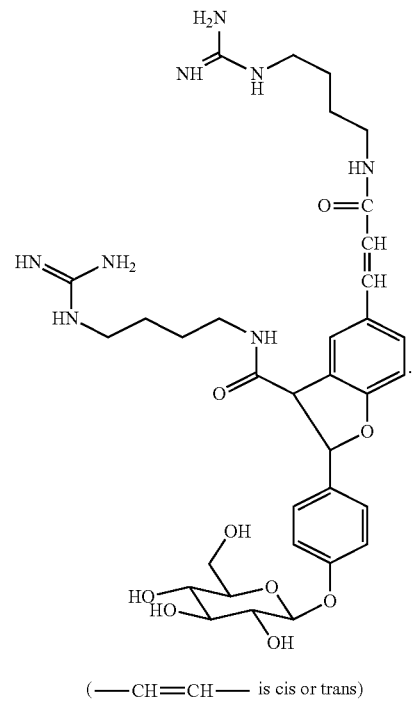

(—CH=CH— is cis or trans)

3. A compound of the following structural formula (III)

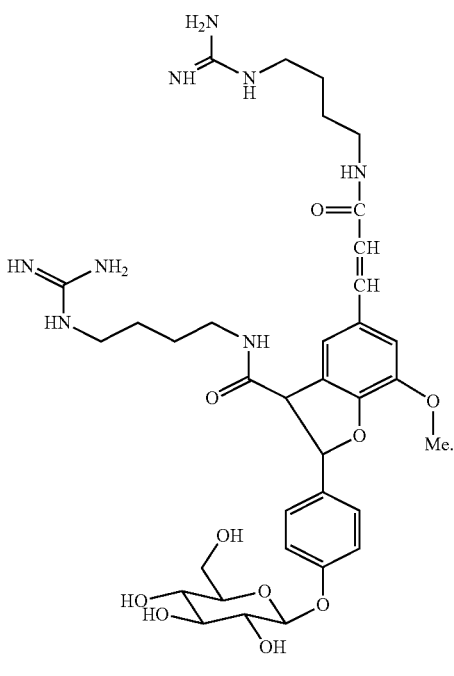

(──CH═CH── is cis or trans, and Me is methyl group)

4. A composition comprising the compound of claim 1, wherein the compound is added in an amount to stimulate oral cavity.

5. The composition of claim 4, wherein the compound is derived from a sprouted cereal grain.

6. A food or drink having added thereto a compound of any one of claim 1, 2, or 3.

7. A food or drink as defined in claim 6, wherein said food or drink is an alcoholic beverage or a nonalcoholic beverage.

8. A food or drink as defined in claim 7, wherein said alcoholic beverage is a malt fermented drink.

9. A composition comprising the compound of claim 2, wherein the compound is added in an amount sufficient to stimulate oral cavity.

10. The composition of claim 9, wherein the compound is derived from a sprouted cereal grain.

11. A composition comprising the compound of claim 3, wherein the compound is added in an amount sufficient to stimulate oral cavity.

12. The composition of claim 10, wherein the compound is derived from a sprouted cereal grain.

13. A method of adjusting a degree of acridness of food and drink comprising admixing the compound of claim 1 or a composition comprising thereof, as an acridness agent, to the food or drink to adjust the degree of acridness.

14. A method of adjusting a degree of acridness of food and drink comprising admixing the compound of claim 2 or a composition comprising thereof, as an acridness agent, to the food or drink to adjust the degree of acridness.

15. A method of adjusting a degree of acridness of food and drink comprising admixing the compound of claim 3 or a composition comprising thereof, as an acridness agent, to the food or drink to adjust the degree of acridness.

* * * * *